(12) United States Patent
Jamison et al.

(10) Patent No.: US 6,863,068 B2
(45) Date of Patent: Mar. 8, 2005

(54) VENTILATION SOUND DETECTION SYSTEM

(75) Inventors: David Thomas Jamison, Quakertown, PA (US); Mark J. Maritch, Bethlehem, PA (US)

(73) Assignee: Draeger Medical, Inc., Telford, PA (US)

(*) Notice: Subject to any disclaimer, the term of this patent is extended or adjusted under 35 U.S.C. 154(b) by 208 days.

(21) Appl. No.: 10/202,952

(22) Filed: Jul. 25, 2002

(65) Prior Publication Data

US 2004/0016434 A1 Jan. 29, 2004

(51) Int. Cl.⁷ ............................................. A61M 16/00
(52) U.S. Cl. ........................ 128/204.23; 128/204.21; 128/205.23
(58) Field of Search .................. 128/204.23, 204.21, 128/205.23; 600/538, 532, 529, 533, 543

(56) References Cited

U.S. PATENT DOCUMENTS

| | | | |
|---|---|---|---|
| 3,333,584 A | | 8/1967 | Andreasen et al. |
| 3,414,896 A | | 12/1968 | Glick et al. |
| 3,513,832 A | * | 5/1970 | Hembrough et al. ........ 600/484 |
| 3,867,934 A | | 2/1975 | Ollivier |
| 4,306,567 A | | 12/1981 | Krasner |
| 4,366,821 A | | 1/1983 | Wittmaier et al. |
| 4,576,178 A | * | 3/1986 | Johnson ...................... 600/483 |
| 4,602,644 A | | 7/1986 | DiBenedetto et al. |
| 5,060,656 A | | 10/1991 | Howard |
| 5,095,900 A | | 3/1992 | Fertig et al. |
| 5,129,401 A | | 7/1992 | Corenman et al. |
| 5,309,921 A | | 5/1994 | Kisner et al. |
| 5,320,093 A | | 6/1994 | Raemer |
| 5,371,854 A | * | 12/1994 | Kramer ...................... 704/270 |
| 5,660,171 A | | 8/1997 | Kimm et al. |
| 5,730,140 A | | 3/1998 | Fitch |
| 5,738,106 A | | 4/1998 | Yamamori et al. |
| 5,836,300 A | | 11/1998 | Mault |
| 5,836,302 A | | 11/1998 | Homuth et al. |
| 5,879,313 A | * | 3/1999 | Raviv et al. ................ 600/595 |
| 5,970,973 A | | 10/1999 | Gonda et al. |
| 6,179,784 B1 | | 1/2001 | Daniels et al. |
| 6,443,907 B1 | * | 9/2002 | Mansy et al. ............... 600/529 |

FOREIGN PATENT DOCUMENTS

| | | |
|---|---|---|
| DE | 41 27 599 A | 2/1993 |
| JP | 61 100231 A | 5/1986 |

OTHER PUBLICATIONS

Govindarajan et al., *International Journal of Clinical Monitoring and Computing*, "Real–time respiratory monitoring workstation—software and hardware engineering aspects," vol. 9, No. 3, pp. 141–148 (Oct. 1992).

\* cited by examiner

*Primary Examiner*—Aaron J. Lewis
(74) *Attorney, Agent, or Firm*—Caesar, Rivise, Bernstein, Cohen & Pokotilow, Ltd.

(57) ABSTRACT

A ventilation sound detection system includes an audible display that emits a series of sounds based upon information provided by a ventilator. In particular, there are two different sound patterns emitted by the system. One sound represents inspiration and the other sound represents expiration. The inspiration sound is enunciated when monitored breathing pressure crosses a threshold level, thereby communicating to an anesthesiologist/clinician that a significant pressure has been developed in the breathing circuit (e.g., a proper inspiration breath has been taken by the patient). The exhalation sound is enunciated when the rising edge of a valid $CO_2$ breath has been returned to the breathing circuit (e.g., a proper exhalation breath has been made). Accordingly, the system provides the anesthesiologist/clinician with a new way of verifying that the patient is being properly ventilated. Therefore, ventilation changes or problems can be identified quickly and effectively.

23 Claims, 4 Drawing Sheets

US 6,863,068 B2

VENTILATION SOUND DETECTION SYSTEM

FIELD OF THE INVENTION

This invention relates to surgery measuring and testing apparatuses, and more particularly to breath analysis, methods and devices for indicating proper respiratory condition, and devices for qualitative and quantitative analysis of breath components.

BACKGROUND OF THE INVENTION

Respiratory monitors and ventilators are known in the art. Typically, ventilators make noises because of pneumatic pressures and flows, and because of the mechanical devices involved. In a traditional operating room, there are various visual alarms that are used as indicia of a patient respiratory rate and depth. Clinicians giving anesthesia are required to monitor the various gauges, displays and screens on an anesthesia machine and the ventilator continuously to ensure that the patient is receiving proper care.

However, these clinicians are busy doing many things during an operation and cannot look at the video monitors, screens, etc. constantly for information on the patient's ventilatory status. Accordingly, it would be advantageous for the clinician to be able to continuously monitor the patient's respiratory characteristics without diverting the clinician's attention from other tasks.

Several patents have tried to solve this problem. U.S. Pat. No. 5,970,973, issued to Gonda et al., discloses a method for delivering insulin lispro. The need for delivering insulin by injection can be reduced by a method whereby an aerolyzed insulin formation is delivered to a patient's lungs. The Gonda et al. patent discloses that in order to carry out an inhale-exhale maneuver of the invention, it is preferable to use a sensor that can signal the patient that a maximal inhale maneuver and a maximal exhale maneuver have been correctly accomplished. The device can issue a common sound when the device has sensed that a maximal inhale maneuver or a maximal exhale maneuver has been accomplished, or the device can flash a green light. The Gonda et al. patent is directed to delivering a sufficient amount of insulin into the bloodstream through inhalation and may require the patient to use a maximum level of both inhalation and exhalation volume.

U.S. Pat. No. 5,836,302, issued to Hometh et al., discloses an audible wave form system for sensing pressure in the patient's airway and emitting an audible wave form based on that pressure. In particular, the system provides a short duration sound in the form of bursts when the pressure of the airway changes by a predetermined incremental amount. A pressure transducer monitors the pressure in the breathing circuit for both inhalation and exhalation, and outputs an audio wave form whenever a certain change in pressure is detected. The frequency of the audible bursts are proportional to the airway pressure so that a particular audible burst will be at the same frequency at the same pressure whether in the inhalation cycle or the exhalation cycle.

U.S. Pat. No. 4,602,644, issued to DiBenedetto et al., discloses a device using a sensor/signal processor that monitors respiration pressure waves and generates corresponding acoustic signals therefrom in a more preferred frequency band. The sensor processor distinguishes between inhalation and exhalation, analyzes the respiration characteristic and uses a pair of thresholds in combination with time monitoring to ensure that inhalation occurred and establish the expected occurrence of exhalation.

U.S. Pat. No. 4,576,178, issued to Johnson, discloses an audio signal generator that can monitor a psychological condition and provide a corresponding audio output signal that varies in correspondence with the monitored psychological condition. U.S. Pat. No. 4,366,821, issued to Wittmaier et al., discloses a breath monitoring device that uses a threshold circuit to differentiate between inhalation and exhalation and which uses a buzzer that emits a common audible sound for failure to meet threshold rates during inhalation and exhalation.

U.S. Pat. No. 3,867,934, issued to Oliver, discloses a pressure monitor that uses high and low limit detectors for monitoring a patient's airway pressures. U.S. Pat. No. 5,730,140, issued to Fitch, discloses a device that utilizes synthesized realistic body sounds that are emitted in accordance with monitored psychological parameters. Moreover, U.S. Pat. No. 5,738,106, issued to Yamamori et al., discloses a device that detects a signal that time varies in accordance with $CO_2$ concentration and a respiration gas, and utilizes a beeper that emits a respective sound depending on the change in $CO_2$ concentration.

However, the prior art does not provide a ventilation sound detection system that emits distinctive sounds for a proper inhalation by a patient and a proper exhalation by the patient by continuously monitoring the patient's inhalation and exhalation. Such a system is needed to impart significant information about the breath delivered and received by the ventilator.

SUMMARY OF THE INVENTION

In an exemplary embodiment, a ventilation sound system of the present invention emits distinctive sounds for a proper inhalation by a patient and a proper exhalation by the patient by continuously monitoring the patient's inhalation and exhalation. The system includes a breathing pressure analyzer, a $CO_2$ analyzer, a processor, and an audio output device. The breathing pressure analyzer detects and measures pressure developed in the system as an inhalation data indicating an inhalation by the patient. The $CO_2$ analyzer detects and measures $CO_2$ developed in the system as an exhalation data indicating an exhalation by the patient. The processor compares the inhalation data to an inhalation threshold and provides a first sound pattern when the inhalation data exceeds the inhalation threshold indicating the proper inhalation. The processor also compares the exhalation data to an exhalation threshold and provides a second sound pattern different than the first sound pattern when the exhalation data exceeds the exhalation threshold indicating the proper exhalation. The audio output device plays the first sound pattern and the second sound pattern.

The processor of this exemplary embodiment may include a threshold manager and a sound manager. The threshold manager determines when the inhalation data indicates a proper inhalation and provides a first signal. The threshold manager also determines when the exhalation data indicates a proper exhalation and provides a second signal. The sound manager provides and outputs the first sound pattern and the second sound pattern to the audio output device.

In another exemplary embodiment of the invention, a ventilation sound system of the present invention that emits distinctive sounds for a proper inhalation by a patient and a proper exhalation by the patient includes a breathing pressure analyzing unit, a $CO_2$ analyzing unit, a processing unit, an audio unit, and an output unit. The breathing pressure analyzing unit measures pressure developed in the system as an inhalation data indicating an inhalation by the patient.

The $CO_2$ analyzing unit measures $CO_2$ developed in the system as an exhalation data indicating an exhalation by the patient. The processing unit compares the inhalation data to an inhalation threshold, and also compares the exhalation data to an exhalation threshold. The audio unit provides a first sound pattern when the inhalation data exceeds the inhalation threshold indicating the proper inhalation. The audio unit also provides a second sound pattern different than the first sound pattern when the exhalation data exceeds the exhalation threshold indicating the proper exhalation. The output unit plays the first sound pattern and the second sound pattern.

In another exemplary embodiment of the invention, a method for playing distinctive sound patterns for a proper inhalation by a patient and a proper exhalation by the patient in accordance with the present invention is disclosed. The method includes measuring breathing pressure as an inhalation data indicating an inhalation by the patient, measuring $CO_2$ as an exhalation data indicating an exhalation by the patient, comparing the inhalation data to an inhalation threshold, providing a first sound pattern when the inhalation data exceeds the inhalation threshold indicating the proper inhalation, comparing the exhalation data to an exhalation threshold, providing a second sound pattern different than the first sound pattern when the exhalation data exceeds the exhalation threshold indicating the proper exhalation, and playing the first sound pattern and the second sound pattern.

Further scope of applicability of the present invention will become apparent in the description given hereafter, however, it should be understood that the detailed description and specific examples, while indicating preferred embodiments of the invention, are given by way of illustration only, since the invention will become apparent to those skilled in the art from this detailed description.

BRIEF DESCRIPTION OF THE DRAWINGS

The invention will be described in conjunction with the following drawings in which like-referenced numerals designate like-elements and wherein.

DETAILED DESCRIPTION OF THE PREFERRED EMBODIMENTS

The ventilation sound detection system includes an audible display that emits a series of sounds based upon information provided by a ventilation monitoring system. In particular, there are two different sound patterns emitted by the system. One sound represents inspiration and the other sound represents expiration. The inspiration sound is enunciated when monitored breathing pressure crosses a threshold level, thereby communicating to an anesthesiologist/clinician that a significant pressure has been developed in the breathing circuit (e.g., a proper inspiration breath has been taken by the patient). The exhalation sound is enunciated when the rising edge of a valid $CO_2$ breath has been returned to the breathing circuit (e.g., a proper exhalation breath has been made).

While not being limited to a particular theory, when active, the system preferably, operates over the range of 3 to 30 breaths per minute. Sound volume and threshold levels can be adjusted as desired. The operator or user can also select from a variety of distinct sounds for the inspiration and expiration patterns. Accordingly, the system provides the anesthesiologist/clinician with a new way of verifying that the patient is being properly ventilated. Therefore, ventilation changes or problems can be identified quickly and effectively.

Figure 1:
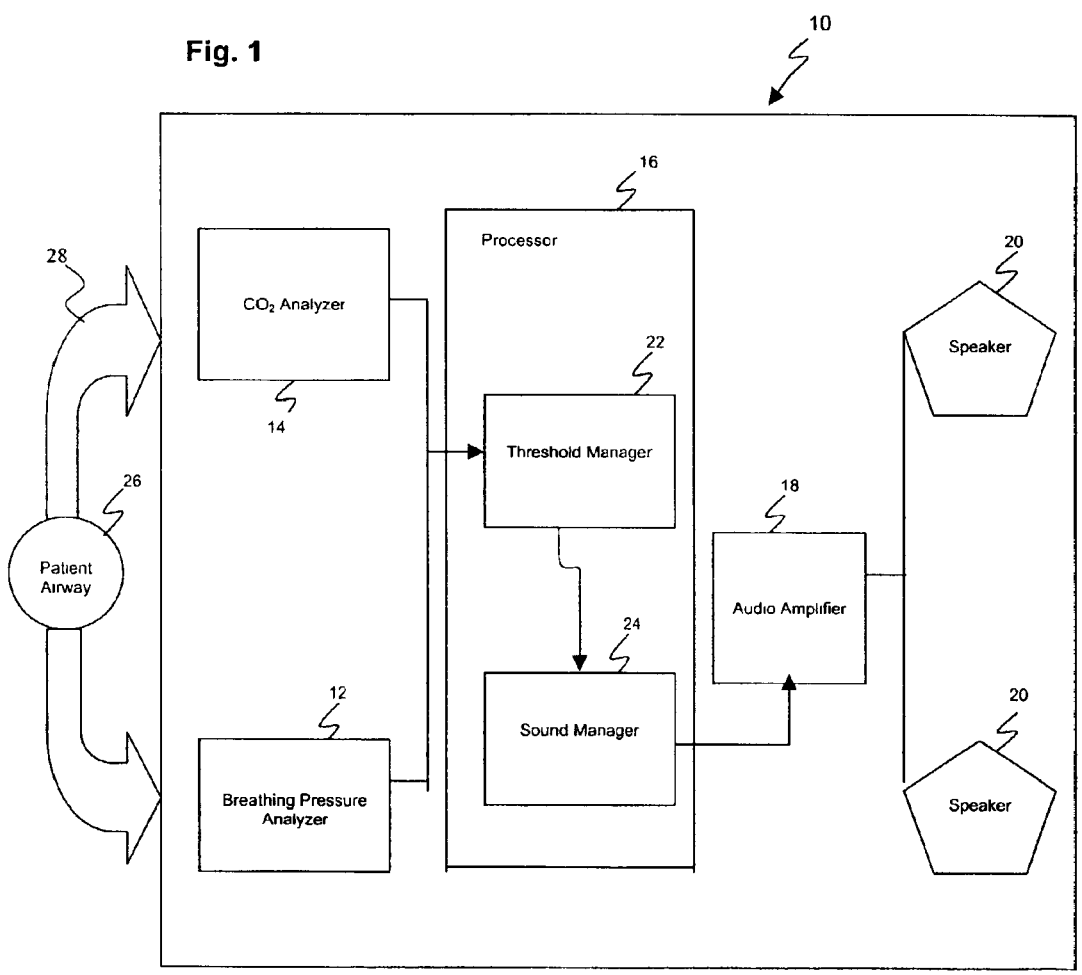
FIG. 1 is a block diagram depicting an exemplary ventilation sound detection system locatable with a ventilator in accordance with a preferred embodiment of the invention.

Referring now in greater detail to the various figures of the application, an exemplary ventilation sound detection system 10 of the invention is illustrated in FIG. 1. The system 10 is preferably part of a ventilator and includes a breathing pressure analyzer 12, a $CO_2$ analyzer 14, a processor 16, an audio amplifier 18 and at least one speaker 20. The processor includes a threshold manager 22 and a sound manager 24.

The system 10 of a ventilator receives respiratory information (e.g., breath samples, breathing pressure differential) from a patient. While not being limited to a particular theory, the respiratory information is preferably received via a patient airway 26 and breathing circuit 28. Both the patient airway 26 and 28 are known in the art as structure that directs respiratory gases between the patient and the ventilation monitoring system.

The breathing pressure analyzer 12 detects and measures pressure in the system 10 as an inhalation data indicating an inhalation by the patient. That is, a differential in breathing pressure, indicative of an inhalation, is forwarded from the breathing circuit 28 to the breathing pressure analyzer 12, which converts the pressure differential into electrical signals via, for example, pressure transducers. The electrical signals provided by the breathing pressure analyzer 12 therefor represent inhalation data indicative of the patient's inhalation. The breathing pressure analyzer 12 is one of many types of gas analyzing units or means that is capable of measuring respiratory flow of an inhalation, as readily understood by a skilled artisan. While not being limited to a particular device or unit, respiratory flow measuring devices or analyzers typically include, but are not limited to, pressure sensors, time of flight devices, ultrasonic doppler units, vortex shedding devices, spinning vanes, or anemometers.

The $CO_2$ analyzer 14 detects and measures $CO_2$ in the system as an exhalation data indicating an exhalation by the patient. The $CO_2$ analyzer 14 converts the sample of patient gas into an electrical signal indicative of the concentration of $CO_2$ in the sample. The signal provided by the $CO_2$ analyzer 14 represents exhalation data indicative of the patient's exhalation. $CO_2$ analyzers that are adapted to measure the partial pressure or amount of carbon dioxide content in a patient's breath are well known. It is understood that the $CO_2$ analyzer 14 is one of many types of analyzing units or means that detects and measures carbon dioxide, as readily understood by a skilled artisan.

The inhalation data and exhalation data are electronically forwarded to the processor 16. The data is preferably forwarded by wire or cable, although other methods know in the art for forwarding electronic signals is within the scope of the invention. The processor 16 may be either a programmed personal computer adapted to receive the signals from the breathing pressure analyzer 12 and the $CO_2$ analyzer 14, or any specially designed processor adapted to compare the inhalation and exhalation data and provide distinct sound patterns as disclosed in greater detail below.

Figure 2:
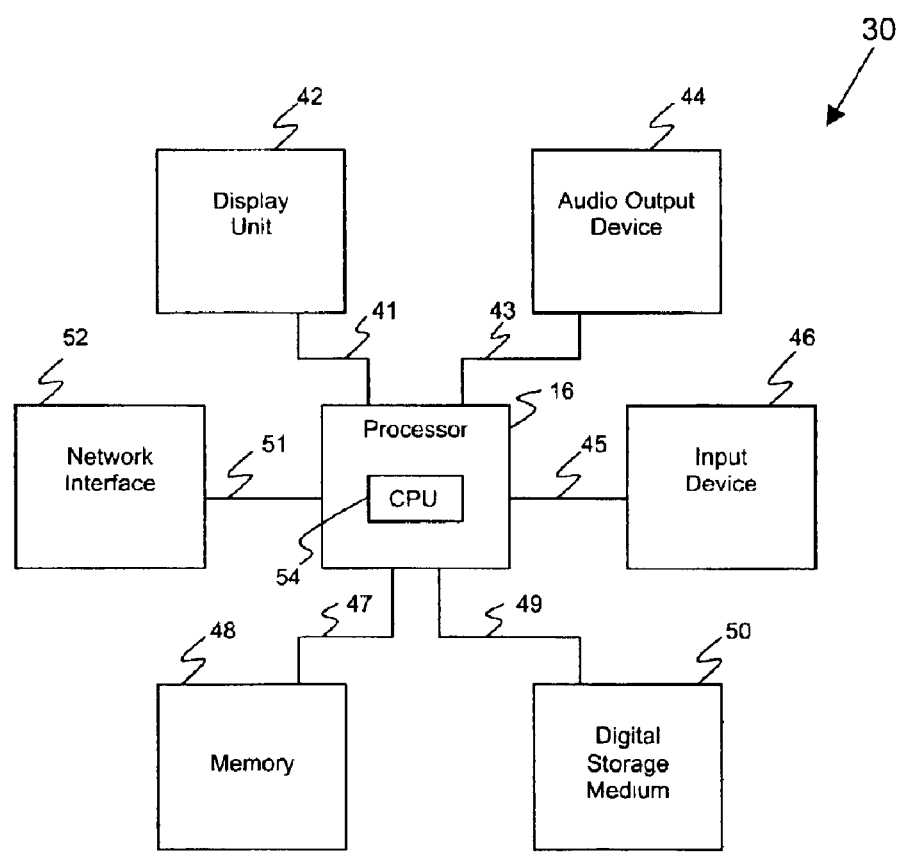
FIG. 2 is a block diagram depicting an exemplary data processing architecture of a computer which supports the ventilation sound detection system in accordance with a preferred embodiment of the invention.

FIG. 2 illustrates a block diagram representing a typical embodiment of a personal computer adapted to support the ventilation sound detection system 10. The computer 30 includes the processor 16 having a central processing unit (CPU) 54 that can process the digital data and other operations required to run the computer 30. It is understood that the task of the CPU 54 can be performed by a single microprocessor or a number of microprocessors.

The exemplary computer 30 also includes a display unit 42 connected via lines 41 to the processor 16. The display unit 42 is preferably a monitor having a size and resolution sufficient to project visual images output via the processor 16 as desired by the clinician. In other words, the display unit 42 is generally a high resolution screen or CRT. An audio output device including, for example, the audio amplifier 18 and speakers 20, is connected via lines 43 to the processor 16 for playing sound pattern as disclosed in greater detail below.

As shown in FIG. 2, the processor 16 is also connected via lines 45 to an input device 46. The input device 46 is preferably a touch screen, but may also may include a keyboard, mouse, microphone, joystick, pen, button, or combination of these devices, depending on how the clinician decides to enter his or her inputs. It is understood that the input device 46 is one or a combination of many types of input units or means for inputting user requests, as readily understood by a skilled artisan.

Still referring to FIG. 2, the processor 16 is also connected via lines 47 to memory 48 via lines 49 to digital storage medium 50, and via lines 51 to a network interface 52. The lines 41, 43, 45, 47, 49, 51 may be physical wires or wireless conduits (e.g., infrared, laser, optical, electrical, etc.).

Memory 48 is in communication with the processor 16 to store and provide data required by the processor to operate the computer 30. The digital storage medium 50 stores electronic instructions and software necessary for addressing and operating the ventilation sound detection system 10 from the computer 30. The digital storage medium 50 can include a hard disk, compact disk, floppy disk, cartridge, network storage unit, any combination thereof, or any other memory capable of storing the electronic instructions and software. The network interface 52 provides a communication medium between the computer 30 and other network devices (e.g., a network server or other medical equipment). The interface 52 can include a modem or a network interface, for example, electrical wire, satellite signal processor, or optical fiber.

Referring back to FIG. 1, as noted above, the processor 16 includes a threshold manager 22 and a sound manager 24. The threshold manager 22 compares the inhalation data to an inhalation threshold to determine when the inhalation data indicates a proper inhalation. Preferably, a proper inhalation occurs when the inhalation data exceeds the inhalation threshold. The inhalation threshold is adjustable by the user or clinician via the input device 46 (FIG. 2), typically between 5 and 30 $cm-H_2O$, although the threshold manager 22 can be adapted to adjust its threshold to other levels. While not being limited to a particular level, the default threshold is preferably set to about 12 $cm-H_2O$.

The threshold manager 22 also compares the exhalation data to an exhalation threshold to determine when the exhalation data indicates a proper exhalation. Preferably, a proper exhalation is indicated when the exhalation data exceeds the exhalation threshold. While not being limited to a particular level, the exhalation threshold is typically about 5 mm-Hg above a mean inspired carbon dioxide level. It is within the spirit of the invention that, if desired, the exhalation threshold could be adjusted by the user or clinician via the input device 46 (FIG. 2).

The threshold manager 22 provides a first signal to the sound manager 24 when the threshold manager 22 determines a proper inhalation. Likewise, the threshold manager 22 forwards a second signal to the sound manager 24 when the threshold manager determines a proper exhalation. It is understood that the threshold manager 22 is one of many types of processor units or means for comparing inhalation data and exhalation data to corresponding thresholds and forwarding corresponding signals when the thresholds are exceeded, as readily understood by a skilled artisan.

The sound manager 24 includes audio software arranged to make the sound manager responsive to the first signal from the threshold manager 22 to output a first sound pattern to the audio output device 44 (FIG. 2). The audio software is also adapted to make the sound manager 24 responsive to the second signal from the threshold manager 22 to provide and output a second sound pattern to the audio output device 44 (FIG. 2). The first sound pattern and the second sound pattern are distinct (e.g., different) from each other. The first sound pattern is from a sound wave file and represents an inspiratory sound preferably selectable by the user or clinician from an inspiratory sound wave file directory located in the digital storage medium 50 (FIG. 2) and accessible to the sound manager 24. Likewise, the second sound pattern is from another sound wave file and represents an expiratory sound preferably selectable by the user or clinician from an expiratory sound wave file directory located in the digital storage medium 50 (FIG. 2) and accessible to the sound manager 24. It is understood that the sound manager 24 is one of many types of audio units or means for providing a first sound pattern upon a proper inhalation and a second sound pattern upon a proper exhalation, as readily understood by a skilled artisan.

The sound manager 24 outputs the first and second sound patterns to the audio output device 44 (FIG. 2), which includes the audio amplifier 18 and speakers 20. The audio amplifier 18 amplifies the sound patterns and outputs the amplified sound patterns to the speakers 20. The speakers 20 change the amplified sound patterns to sound, thereby audiblizing the sound pattern to the user or clinician.

The input device 46 preferably includes a volume control that allows the user or clinician to adjust the amplification of the distinct sound patterns by the audio amplifier to a sound volume preferred by the clinician. Moreover, the system 10 allows the user or clinician to choose from a palette of sound pairs, one of each pair from the inspiration sound wave file and one from the expiratory sound wave file, allowing the clinician to personalize the workplace, that is, listen to sound patterns that he or she prefers. The system 10 allows the clinician to feel confident that the patient is being ventilated, thereby enhancing the level of the clinician's vigilance since ventilation changes or problems can be detected quickly via this auditory display. Preferably, the ventilation sound detection system 10 enunciates distinct sound patterns indicating proper inhalation and exhalation over the range of 3 to 30 breaths per minute.

It is understood that the audio amplifier 18 is a type of amplifying wit or means for increasing the magnitude of input sound patterns into amplified sound patterns, as readily understood by a skilled artisan. Likewise it is understood that a speaker 20 is a type of audible wit or means for emitting sound based on amplified sound patterns, as readily understood by a skilled artisan. Moreover, it is understood that the output device 44 is one type of output unit or means for playing sound patterns, as readily understood by a skilled artisan.

Figure 3:
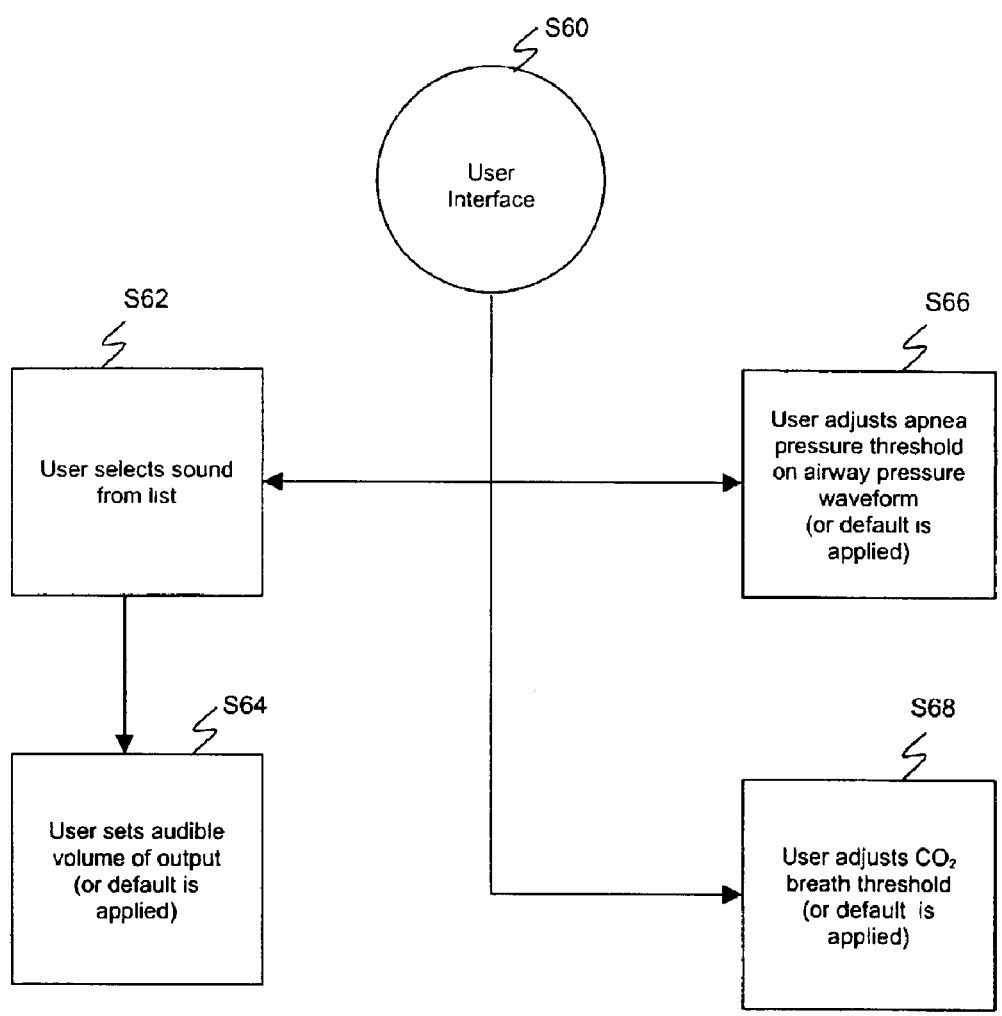
FIG. 3 is an exemplary flowchart illustrating steps for modifying sound and threshold parameters in accordance with a preferred embodiment of the invention.

FIG. 3 illustrates options available to the clinician via the input device 46 (FIG. 2). At step S60, the clinician interfaces with the input device 46. Using this interface, the clinician can select pairs of distinct sounds from a list of sounds typically stored in the digital storage medium 50 (FIG. 2). After selecting a pair of distinct sounds from the list at step S62, the clinician can set the audible volume of the sound at step S64. If the clinician does not set the audible volume, then a default volume may be applied that audiblizes the sound at a reasonable volume. At step S66, the clinician can adjust the inhalation threshold (e.g., apnea pressure threshold) from the default threshold of about 12 cm-$H_2O$ within a preferred range of about 5 to 30 cm-$H_2O$. While not being limited to a particular theory, this sound system is adaptable to allow the clinician the capability to also adjust the exhalation threshold or $CO_2$ breath threshold from the default threshold of about 5 mm-Hg above a mean inspired $CO_2$ level to a level preferred by the clinician for the patient, at step S68.

Figure 4:
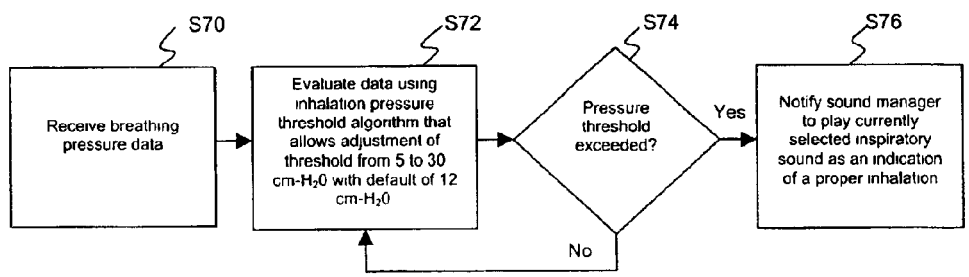
FIG. 4 shows an exemplary flowchart illustrating steps used in operation of a ventilation sound detection system of the invention.

FIG. 4 illustrates steps taken by the threshold manager 22 (FIG. 1) in accordance with an exemplary embodiment of the invention. At step S70, the threshold manager 22 receives breathing pressure data from the breathing pressure analyzer 12. The threshold manager 22 evaluates the breathing pressure data using an inhalation pressure threshold algorithm that allows adjustment of the threshold from 5 to 30 cm-$H_2O$ with a default threshold preferably set at 12 cm-$H_2O$. The inhalation pressure threshold algorithm is part of the software used by the threshold manager 22 for determining when the inhalation data indicates a proper inhalation. Accordingly, it is understood that the software is adapted to drive the functions of the threshold manager 22, as readily understood by a skilled artisan.

The threshold manager 22 compares the breathing pressure data to the inhalation pressure threshold at step S74 and provides a signal notifying the sound manager 24 (FIG. 1) to play the currently selected inspiratory sound as an indication of a proper inhalation at step S76. If the threshold manager 22 determines that the inhalation pressure threshold is not exceeded by the current breathing pressure data at step S74, then the threshold manager 22 evaluates the next available breathing pressure data forwarded from the breathing pressure analyzer 12 (FIG. 1).

Figure 5:
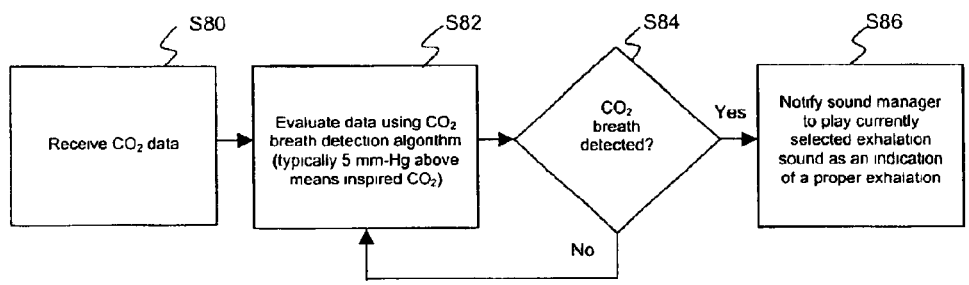
FIG. 5 shows an exemplary flowchart illustrating steps used in operation of a ventilation sound detection system of the invention.

FIG. 5 is a flowchart illustrating exemplary steps taken by the threshold manager 22 (FIG. 1) for determining when the exhalation data indicates a proper exhalation, in accordance with the exemplary embodiments. At step S80, the threshold manager 22 receives $CO_2$ data from the $CO_2$ analyzer 14. The threshold manager 22 evaluates the $CO_2$ data using a $CO_2$ breath detection algorithm having a threshold typically set at about 5 mm-Hg above the mean inspired $CO_2$ level of the patient. The $CO_2$ breath detection algorithm is preferably part of the software used by the threshold manager 22 in determining the proper exhalation.

At step S84, the threshold manager 22 compares the received $CO_2$ data to the exhalation threshold to detect a proper exhalation if the $CO_2$ data exceeds the exhalation threshold. If the $CO_2$ data exceeds the exhalation threshold, the threshold manager 22 provides a second signal notifying the sound manager 24 to play the currently selected exhalation sound, which is distinct from the inspiratory sound at step S86. If, at step S84, the threshold manager 22 determines that a proper exhalation did not occur, then the threshold manager 22 evaluates the next available exhalation data from the $CO_2$ analyzer 14 at step S82.

It should be apparent from the aforementioned description and the attached drawings that the concept of the present application may be readily applied to a variety of preferred embodiments, including the exemplary embodiments disclosed herein. Without further elaboration, the foregoing will so fully illustrate the invention that others may, by applying current or future knowledge, readily adapt the same for use under various conditions of service.

What is claimed is:

1. A ventilation sound system that emits distinctive sounds for a proper inhalation by a patient and a proper exhalation by the patient by continuously monitoring the patient's inhalation and exhalation, the system comprising:
   a breathing pressure analyzer that detects and measures pressure in the system as an inhalation data indicating an inhalation by the patient;
   a $CO_2$ analyzer that detects and measures $CO_2$ in the system as an exhalation data indicating an exhalation by the patient;
   a processor that compares the inhalation data to an inhalation threshold and provides a first sound pattern when the inhalation data exceeds the inhalation threshold indicating the proper inhalation, said processor also comparing the exhalation data to an exhalation threshold and providing a second sound pattern different than the first sound pattern when the exhalation data exceeds the exhalation threshold indicating die proper exhalation; and
   an audio output device responsive to the processor to play the first sound pattern and the second sound pattern.

2. The ventilation sound system of claim 1, said audio output device comprising
   an audio amplifier that increases the magnitude of the first sound pattern into an amplified first sound pattern and that increases the magnitude of the second sound pattern into an amplified second sound pattern, and
   at least one speaker that emits the amplified first sound pattern as a first sound and that emits the amplified second sound pattern as a second sound.

3. The ventilation sound system of claim 1, further comprising an input device connected to said processor and responsive to user input to adjusts the inhalation threshold based on the user input.

4. The ventilation sound system of claim 3, said input device further responsive to the user input to select a first sound pattern and a second sound pattern based on the user input.

5. The ventilation sound system of claim 3, said input device further responsive to the user input to select a volume for outputting the first sound pattern and the second sound pattern based on the user input.

6. The ventilation sound system of claim 1, said processor including a threshold manager that determines when the inhalation data indicates a proper inhalation and provides a first signal, said threshold manager further determines when the exhalation data indicates a proper exhalation and provides a second signal, and a sound manager responsive to the first signal to provide and output the first sound pattern to the audio output device, said sound manager also responsive to the second signal to provide and output the second sound pattern to the audio output device.

7. The ventilation sound system of claim 1, wherein the inhalation threshold is less than a maximum inhalation level, and the exhalation threshold is less than a maximum exhalation level.

8. The ventilation sound system of claim 1, wherein the first sound pattern and the second sound pattern are generally unrelated to bodily sounds.

9. A ventilation sound system that emits distinctive sounds for a proper inhalation by a patient and a proper exhalation by the patient by continuously monitoring the patient's inhalation and exhalation, the system comprising:

breathing pressure analyzing means for measuring pressure in the system as an inhalation data indicating an inhalation by the patient;

$CO_2$ analyzing means for measuring $CO_2$ in the system as an exhalation data indicating an exhalation by the patient;

processing means for comparing the inhalation data to an inhalation threshold and for comparing the exhalation data to an exhalation threshold;

audio means for providing a first sound pattern when the inhalation data exceeds the inhalation threshold indicating the proper inhalation, and for providing a second sound pattern different than the first sound pattern when the exhalation data exceeds the exhalation threshold indicating the proper exhalation; and output means responsive to said audio means for playing the first sound pattern and the second sound pattern.

10. The ventilation sound system of claim 9, said output means comprising amplifying means for increasing the magnitude of the first sound pattern into an amplified first sound pattern and for increasing the magnitude of the second sound pattern into an amplified second sound pattern, and audible means for emitting the amplified first sound pattern as a first sound and for emitting the amplified second sound pattern as a second sound.

11. The ventilation sound system of claim 9, further comprising input means responsive to user input for adjusting the inhalation threshold based on the user input.

12. The ventilation sound system of claim 11, said input means further responsive to the user input for selecting a first sound pattern and a second sound pattern based on the user input.

13. The ventilation sound system of claim 11, said input means further responsive to the user input for selecting a volume for emitting the amplified first sound pattern and the amplified second sound pattern based on the user input.

14. The ventilation sound system of claim 9, said processing means providing a first signal when the inhalation data indicates a proper inhalation and provides a second signal when the exhalation data indicates a proper exhalation, said audio means responsive to the first signal to output the first sound pattern to said output means, and also responsive to the second signal to output the second sound pattern to said output means.

15. The ventilation sound system of claim 9, wherein the inhalation threshold is less than a maximum inhalation level, and the exhalation threshold is less than a maximum exhalation level.

16. The ventilation sound system of claim 9, wherein the first sound pattern and the second sound pattern are generally unrelated to bodily sounds.

17. A method for playing distinctive sound patterns for a proper inhalation by a patient and a proper exhalation by the patient, the method comprising:

measuring breathing pressure as an inhalation data indicating an inhalation by the patient;

measuring $CO_2$ as an exhalation data indicating an exhalation by the patient;

comparing the inhalation data to an inhalation threshold;

providing a first sound pattern when the inhalation data exceeds the inhalation threshold indicating the proper inhalation;

comparing the exhalation data to an exhalation threshold;

providing a second sound pattern different than the first sound pattern when the exhalation data exceeds the exhalation threshold indicating the proper exhalation; and playing the first sound pattern and the second sound pattern.

18. The method of claim 17, wherein playing the first sound pattern and the second sound pattern includes increasing the magnitude of the first sound pattern into an amplified first sound pattern, increasing the magnitude of the second sound pattern into an amplified second sound pattern, emitting the amplified first sound pattern as a first sound, and emitting the amplified second sound pattern as a second sound.

19. The method of claim 17, further comprising adjusting the inhalation threshold based on user input.

20. The method of claim 17, further comprising selecting a first sound pattern and a second sound pattern based on user input.

21. The method of claim 17, further comprising selecting a volume for emitting the amplified first sound pattern and the amplified second sound pattern based on user input.

22. The method of claim 17, wherein the inhalation threshold is less than a maximum inhalation level, and the exhalation threshold is less than a maximum exhalation level.

23. The method of claim 17, wherein the step of providing the first sound pattern includes providing the first sound pattern generally unrelated to bodily sounds and the step of providing the second sound pattern includes providing the second sound pattern generally unrelated to bodily sounds.

* * * * *